United States Patent [19]

Collier, Jr.

[11] Patent Number: 5,545,234

[45] Date of Patent: Aug. 13, 1996

[54] LOWER EXTREMITY PROSTHETIC DEVICE

[76] Inventor: Milo S. Collier, Jr., 1152 Douglas St., Longview, Wash. 98632

[21] Appl. No.: 332,655

[22] Filed: Nov. 1, 1994

Related U.S. Application Data

[63] Continuation of Ser. No. 74,101, Jun. 8, 1993, abandoned, which is a continuation-in-part of Ser. No. 680,310, Apr. 4, 1991, Pat. No. 5,314,499.

[51] Int. Cl.$^6$ .................................................. A61F 2/66
[52] U.S. Cl. ................................. 623/49; 623/52; 623/55
[58] Field of Search .................................. 623/53, 48, 49, 623/55, 47, 50–52, 54

[56] References Cited

U.S. PATENT DOCUMENTS

| | | |
|---|---|---|
| 419,019 | 1/1890 | Kolbe .................................. 623/53 X |
| 579,009 | 3/1897 | Richen . |
| 584,004 | 6/1897 | Lyons . |
| 598,230 | 2/1898 | Roberts et al. . |
| 648,345 | 4/1900 | Peer .................................. 623/53 X |
| 714,052 | 11/1902 | Staggs . |
| 757,287 | 4/1904 | Duggan . |
| 810,180 | 1/1906 | Wintermute . |
| 1,023,247 | 4/1912 | Frees . |
| 1,071,230 | 8/1913 | Hunger .............................. 623/54 X |
| 1,090,327 | 3/1914 | Milligan . |
| 1,151,520 | 8/1915 | Hanger . |
| 1,294,632 | 2/1919 | Dickson . |
| 1,319,471 | 10/1919 | Giebeler-Wanke . |
| 1,698,372 | 1/1929 | McElroy . |
| 1,804,915 | 5/1931 | Collins . |
| 1,995,442 | 3/1935 | Wolfe . |
| 2,036,830 | 4/1936 | Rowley . |
| 2,126,654 | 8/1938 | Morris . |
| 2,130,271 | 9/1938 | Eastham . |
| 2,197,093 | 4/1940 | Campbell . |
| 2,289,154 | 7/1942 | Van Cise . |
| 2,416,817 | 3/1947 | Carter . |
| 2,442,151 | 5/1948 | Strickland . |
| 2,443,356 | 6/1948 | Mathis . |
| 2,446,042 | 7/1948 | Valenti . |
| 2,450,728 | 10/1948 | Havens ................................ 623/44 |
| 2,453,969 | 11/1948 | Carter . |
| 2,470,480 | 5/1949 | Fogg . |
| 2,475,372 | 7/1949 | Catranis . |
| 2,475,373 | 7/1949 | Catranis . |
| 2,490,806 | 12/1949 | Henschke et al. . |
| 2,551,724 | 5/1951 | Campbell . |
| 2,570,735 | 10/1951 | Weise . |
| 2,594,752 | 4/1952 | Fahlström .......................... 623/47 |
| 2,605,475 | 8/1952 | Burger et al. . |
| 2,620,485 | 12/1952 | Greissinger . |
| 2,644,165 | 7/1953 | Grisoni . |
| 2,687,533 | 8/1954 | McCormick . |
| 2,692,392 | 10/1954 | Bennington et al. . |
| 2,699,554 | 1/1955 | Comelli . |
| 2,731,645 | 1/1956 | Woodall . |
| 2,745,108 | 5/1956 | Withers . |
| 3,480,972 | 12/1969 | Prahl . |

(List continued on next page.)

FOREIGN PATENT DOCUMENTS

| | | | |
|---|---|---|---|
| 0922990 | 6/1947 | France ................................... 623/53 |
| 0325333 | 9/1920 | Germany .............................. 623/53 |
| 0807214 | 6/1951 | Germany .............................. 623/55 |
| 0817186 | 10/1951 | Germany .............................. 623/53 |
| 0443017 | 1/1950 | Italy ...................................... 623/55 |
| 0848023 | 7/1981 | U.S.S.R. ............................... 623/53 |
| 1409258 | 7/1988 | U.S.S.R. ............................... 623/55 |
| 2092451 | 8/1982 | United Kingdom ................... 623/53 |

*Primary Examiner*—David H. Willse
*Attorney, Agent, or Firm*—Kolisch, Hartwell, Dickinson, McCormack & Heuser

[57] ABSTRACT

A lower extremity prosthetic device is provided which includes a modular foot with a heel section and an elongate midfoot section, the heel and midfoot sections being configured for detachable combination via a coupling joint. The heel section is formed from a material of a first predetermined stiffness characteristic and the midfoot section is formed from a material of a second predetermined stiffness characteristic, providing a foot of a differential stiffness characteristic akin to that of a natural foot.

10 Claims, 2 Drawing Sheets

U.S. PATENT DOCUMENTS

| | | |
|---|---|---|
| 3,538,516 | 11/1970 | Bailey et al. . |
| 3,551,914 | 1/1971 | Woodall . |
| 3,754,286 | 8/1973 | Ryan . |
| 3,766,569 | 10/1973 | Orange . |
| 3,874,004 | 4/1975 | May . |
| 3,982,280 | 9/1976 | Asbelle et al. . |
| 4,007,497 | 2/1977 | Haupt . |
| 4,177,525 | 12/1979 | Arbogast et al. . |
| 4,180,872 | 1/1980 | Chaikin . |
| 4,328,594 | 5/1982 | Campbell et al. . |
| 4,360,931 | 11/1982 | Hampton . |
| 4,364,128 | 12/1982 | Mummert . |
| 4,446,580 | 5/1984 | Furuya et al. . |
| 4,547,913 | 10/1985 | Phillips . |
| 4,605,417 | 8/1986 | Fleischauer . |
| 4,619,661 | 10/1986 | Axelsson . |
| 4,636,220 | 1/1987 | Ziegelmeyer . |
| 4,645,509 | 2/1987 | Poggi et al. . |
| 4,652,266 | 3/1987 | Truesdell . |
| 4,721,510 | 1/1988 | Cooper et al. . |
| 4,822,363 | 4/1989 | Phillips . |
| 4,865,612 | 9/1989 | Arborgast et al. . |
| 4,938,776 | 7/1990 | Masinter . |
| 4,959,073 | 9/1990 | Merlette . |
| 5,116,384 | 5/1992 | Wilson et al. ............... 623/49 |

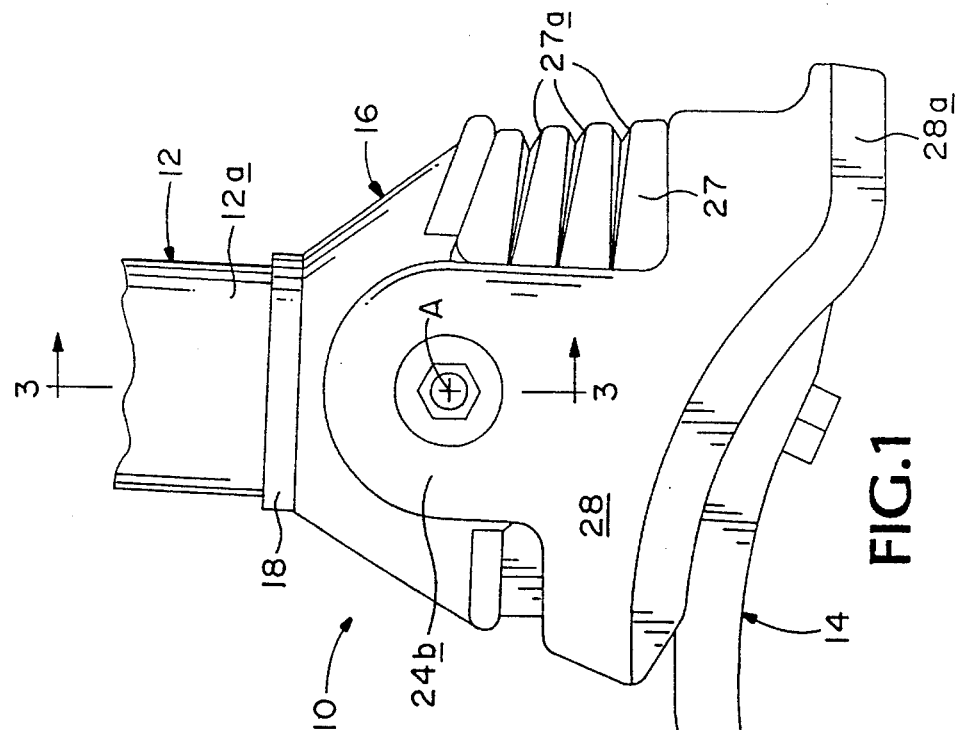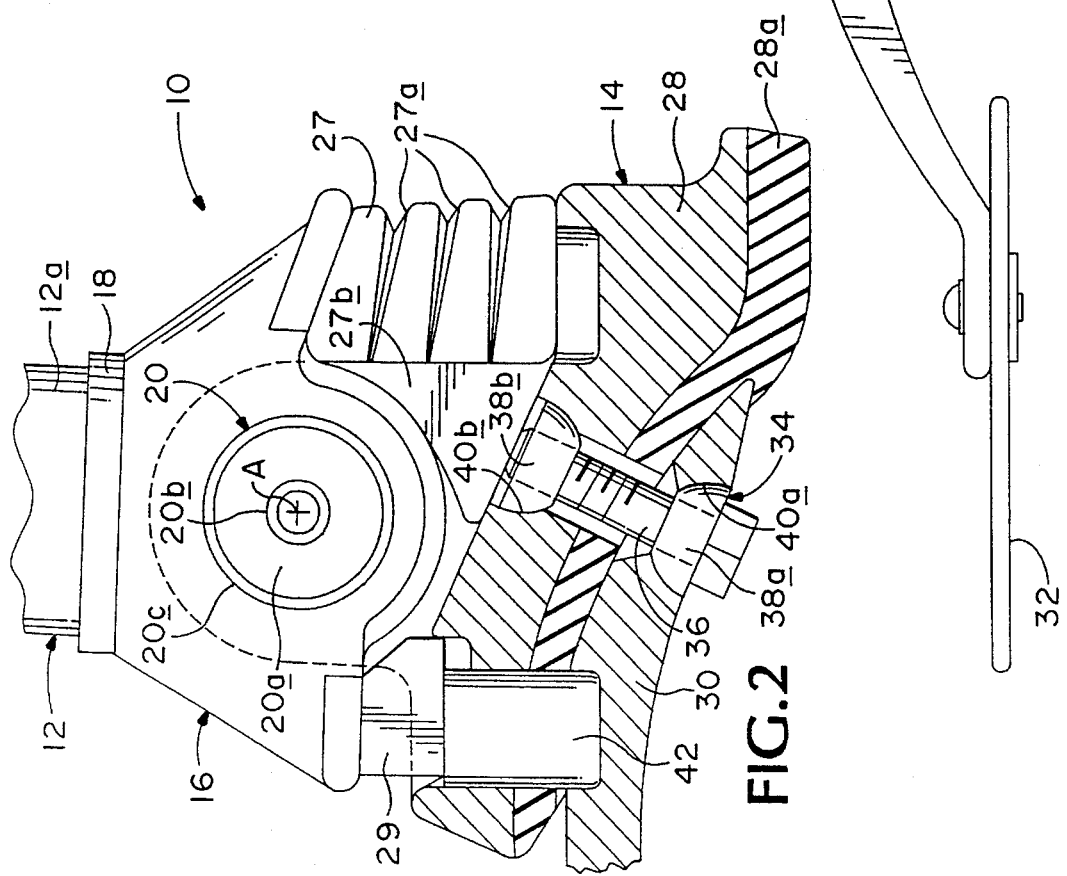

5,545,234

LOWER EXTREMITY PROSTHETIC DEVICE

This is a continuation of U.S. patent application Ser. No. 08/074,101, filed on Jun. 8, 1993, now abandoned, which is a continuation-in-part of U.S. patent application Ser. No. 07/680,310, filed on Apr. 4, 1991, now U.S. Pat. No. 5,314,499.

TECHNICAL FIELD

This invention relates generally to prosthetic devices, and more particularly to a prosthesis for use by lower extremity amputees. The invented prosthesis includes an artificial ankle and foot, and may further include an artificial shin and knee. A modular design is used, allowing for user-specific prosthesis construction, accommodating the repair of individual components, and giving the device characteristics which are more similar to the characteristics of a natural limb.

BACKGROUND ART

A prosthetic device or prosthesis is an artificial substitute for a part of the body such as a limb. Numerous prostheses have been developed to serve this purpose, each trying to replicate the function and appearance of the missing body part.

Lower leg prosthetic devices present unique problems. They must be strong enough to support the weight of a person and to withstand the forces encountered when walking or running, but they must also be light enough to allow comfortable use. This dichotomy is further complicated by the increasing number of lower-limb amputees who desire to participate in athletic activities, such activities requiring the use of prosthetic devices which have mobility which is very similar to the amputee's original limb. Lower leg prosthetic devices must be similar enough in mobility to natural legs to accommodate athletic activity while remaining both strong and comfortable to the user. The invented artificial limb addresses those problems.

DISCLOSURE OF THE INVENTION

The invented lower extremity prosthetic device includes a modular foot which has a heel section and an elongate midfoot section configured for detachable combination via a coupling joint. The heel section is formed from a material of a first predetermined stiffness characteristic and the midfoot section is formed from a material of a second predetermined stiffness characteristic, providing a foot of a differential stiffness characteristic akin to that of a natural foot. In the preferred embodiment, the prosthetic device further includes a toe section of a third predetermined stiffness characteristic, the toe section being removably coupled with the midfoot section to make the prosthesis even more similar to a natural foot.

The heel and midfoot sections are configured for selected relative movement via a coupling joint which includes a rigid pin with arcuate half-spheres mounted in a ball-and-socket-like arrangement to each of the heel and midfoot sections. A resilient pin is interposed the midfoot and heel sections to limit, but not completely restrict, pivot of the midfoot section relative to the heel section.

An ankle member is preferably coupled with the foot, the ankle member being capable of rotation about an axis which is substantially perpendicular to a longitudinal line connecting the toe and heel sections of the foot. This is accomplished via a bearing arrangement which includes a resilient internal body surrounded by less-resilient inner and outer annular shells. A spring element is interposed the ankle and foot so as to yieldably urge the ankle and foot into a predetermined relative orientation. The foot is thus capable of motion which is similar to the motion of the user's natural foot.

BRIEF DESCRIPTION OF THE DRAWINGS

FIG. 1 is a fragmentary side view of a prosthesis constructed in accordance with the present invention.

FIG. 2 is a partially sectioned view of the prosthesis depicted in FIG. 1, such view illustrating the construction of the prosthesis' heel.

DETAILED DESCRIPTION AND BEST MODE FOR CARRYING OUT THE INVENTION

Figure 3:
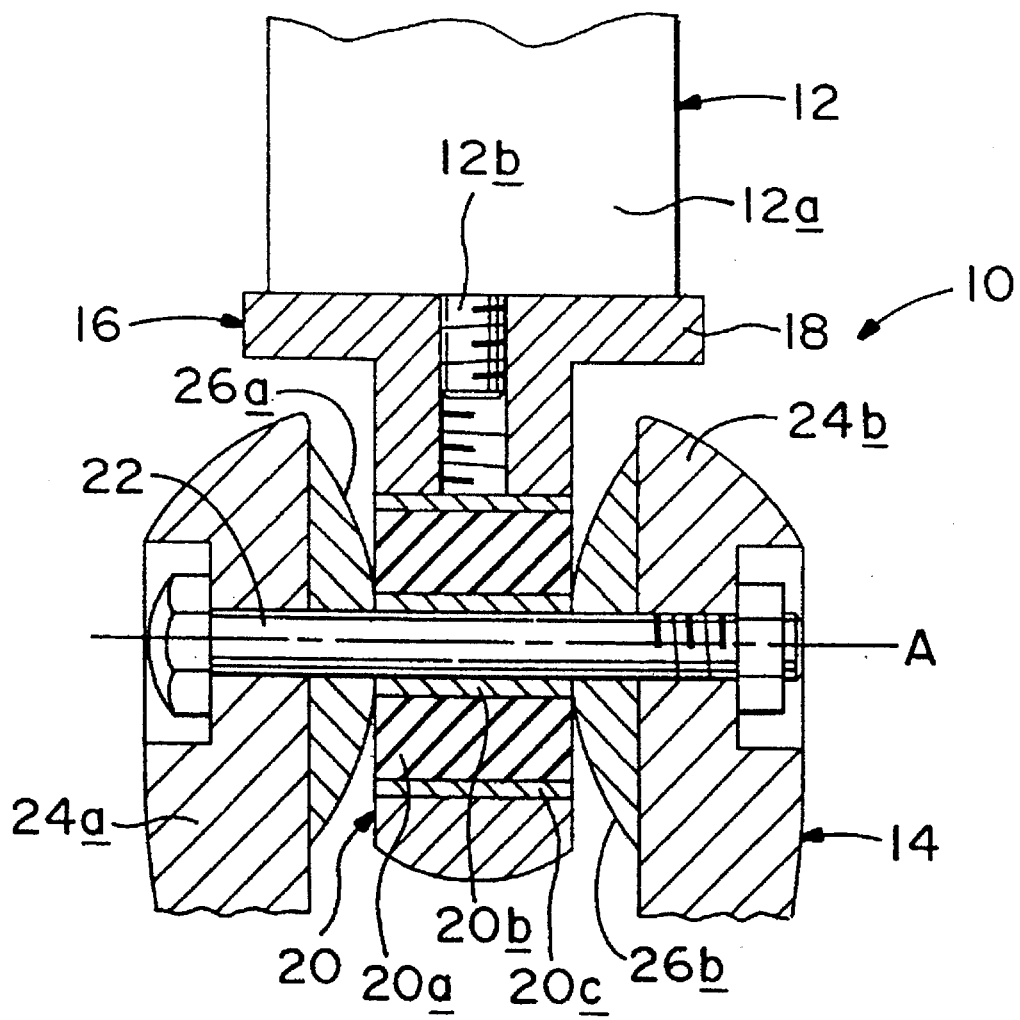
FIG. 3 is a sectional view of the prosthesis taken along lines 3—3 of FIG. 1, back plan view of the invented limb.

A preferred embodiment of the invented prosthetic device is shown in FIGS. 1 through 3 with the device being indicated generally at 10. As indicated, the prosthetic device is readily divided into three members, an artificial shin member 12, an artificial foot member 14, and an artificial ankle member 16. In some instances, the device further includes an artificial knee member (not shown), allowing for use by above-the-knee amputees. Although not shown, it will be appreciated that the prosthetic device will commonly be covered by a material such as rubber which is intended to simulate skin.

Referring initially to shin member 12, it will be noted that such shin is an elongate member, including a first end 12a and a second end (not shown). As shown in FIG. 3, the first end of the shin is secured to a mount 18, such mount including a bore sized and shaped so as to receive a bolt 12b which forms a part of the shin. The second end of the shin is similarly secured to an amputation socket or knee (neither of which is shown). In order to compensate for variances in the physical characteristics of the prosthesis user, the shin can be laterally off-set relative to the center user's amputation socket or knee.

It is to be understood that although one embodiment of the shin and mount combination is shown, the shin and mount used may similarly take other suitable forms, including the form of the shin and mount described in my above-identified co-pending patent application entitled "An Artificial Limb Including a Shin, Ankle and Foot". This arrangement offers particular benefits as described in that application.

In the preferred embodiment, the shin is constructed from a nylon polymer or carbon graphite, the material used often depending on the type of knee or socket with which it is to be used. These materials have some flexibility, but are strong enough to support the weight of a user. Additionally, the shin may be in the form of a tube, with the inner diameter of the tube selected to achieve different strengths and flexibilities. Alternatively, an aluminum or titanium tube may be used, but these materials provide a less flexible shin.

The flexibility of shin 12 allows for torsional or rotary movement of the ankle and foot, such action creating a more comfortable prosthesis because it reduces the pressure applied to the tissue at an amputation site. That advantage is particularly helpful in fitting a prosthesis to an older amputee. The flexibility of the shin also permits some forward/ backward and side-to-side movement, adding to the mobility of the ankle and foot as will be described below.

As shown in the drawing figures, and as previously indicated, shin 12 is connected to foot 14 by ankle 16, such ankle being integrally formed with mount 18 in the embodiment shown. The ankle, it will be appreciated, includes an annular bearing element 20 which allows for rotation about an axis A. Axis A is defined along the length of a pin 22 which extends between a pair of arms 24a, 24b which are formed as a part of the foot member. The arms extend upwardly on opposite sides of the foot to capture a downwardly extending portion of ankle 16. Pin 22 acts as an axle for relative rotation of the ankle and foot, the pin passing through tight-fitting bores in arms 24a and 24b and through an oversized bore in the bearing of ankle 16. In the preferred embodiment, the pin extends through holes in the arms and is readily removable so as to accommodate separation of the ankle and foot for performing repairs.

In order to accommodate flexion and dorsi-flexion of the foot, the bearing includes an annular resilient internal body 20a formed of a material such as rubber, making the bearing compressible under the weight of a user of average size. A less resilient inner shell 20b and similar less resilient outer shell 20c provide structure and longevity to the bearing. These shells are tubular and are constructed from a smooth and generally rigid material such as aluminum so as to accommodate rotation of the ankle about axis A. The bearing is engaged on opposite sides by washers 26a, 26b which define convex surfaces against which the ankle pivots side-to-side. Because the bearing is of annular construction, it will be appreciated that pivot of the ankle is akin to rotary pivot of a universal joint (i.e., pivot about orthogonal axes). The lateral rotation of the ankle is restricted by the density of resilient internal body 20a. The action provided by the invented prosthesis is thus similar to the action provided by a natural ankle, rotary motion of the foot being allowed.

Because different individuals require different degrees of mobility (i.e., an athlete requires more mobility than a more sedentary person), the material which forms internal body 20a may be chosen according to the user's particular needs. Similarly, the curvature of the washers which aid in defining side-to-side pivot of the foot may be chosen according to the needs of the individual involved. Where side-to-side pivot is less desirable, washers with flat surfaces may be chosen in order to greatly restrict unwanted pivot of the foot.

A spring element 27 is mounted intermediate the foot and ankle, such spring element tending to urge the ankle to pivot counterclockwise to its position in FIG. 2. The pivot force exerted by spring element 27, however, is opposed by resilient cushion 29 which acts on the opposite end of the ankle as shown. Both the spring element and the resilient cushion are preferably formed from a material such as foam rubber, providing yieldable resistance to pivot of the ankle about axis A. In the preferred embodiment, spring element 27 takes a bellows-like shape, including a series of grooves 27a. This shape, it will be appreciated, will tend to reduce the element's bulge under compression and will extend spring life due to the absence of such bulge. A lever portion 27b is interposed the ankle member (in the vicinity of the bearing arrangement) and the foot member (in the vicinity of the heel section), such lever portion tending to urge the foot and ankle apart.

Referring now to foot member 14, it will be noted that such foot member is of a modular construction, including a heel section 28, a midfoot section 30 and a toe section 32. Such sections are removably coupled with one another, allowing for easy disassembly and repair. Because the foot is modular, it will be appreciated that it is possible to construct a foot which has particular flex characteristics, such characteristics being dependent on the shape of the individual sections and on the materials used to form such sections.

The heel section, it will be noted, is typically formed from a relatively rigid material such as glass-reinforced nylon or carbon graphite composite. Such section, it will be noted, is generally constructed in an arch. The midfoot section, which is also arch-shaped, is preferably formed of a more resilient material, the flexibility of the materials chosen and the arched shape of the heel-midfoot combination allowing the foot member to act as an energy storage spring that absorbs energy on impact and that helps raise the foot during walking. The toe section may be even more resilient, emulating the flexibility of natural toes. In order to further the spring effect of the foot, an elongate cushion 28a is applied to the heel section in the area of interface between the heel and midfoot sections.

Looking now to FIG. 2, and focussing attention on the mechanism by which the heel section and midfoot sections are combined, it will be appreciated that such combination is achieved via a coupling joint such as universal-joint-like arrangement 34. As shown, arrangement 34 includes an elongate rigid pin 36 which is threaded to receive half-spheres 38a, 38b on opposite ends thereof. The half-spheres have facing arcuate surfaces, each of which is suited for journaling in corresponding sockets 40a, 40b, respectively. The half-spheres slide within the sockets so as to allow limited fluid movement of the midfoot section relative to the heel section in a manner similar to that of a ball-and-socket.

A flexible pin 42 further restricts movement of the midfoot section relative to the heel section, such flexible pin being received by both the heel and midfoot sections at a position spaced from rigid pin 36. In the preferred embodiment, flexible pin 42 is formed from a lightweight, resilient material such as foam rubber or the like. The flexible pin will thus serve to urge the heel and midfoot sections into the predetermined relative orientation shown in FIG. 2, but will allow relative movement under the weight of a user as required.

INDUSTRIAL APPLICABILITY

The invented artificial limb is applicable to the prosthesis industry generally and is specifically designed for lower limb amputees. While the preferred embodiment of the invention has been described, it will be appreciated that variations and alterations may be made without departing from the spirit and scope of the invention as defined by the appended claims.

I claim:

1. A lower extremity prosthetic device comprising:
   a modular foot member which includes a molded heel section formed substantially from a structural material of a first predetermined modulus of elasticity and an elongate molded midfoot section which extends, in cantilever fashion, forwardly from said heel section in an arc, said midfoot section being formed substantially from a structural material having a second predetermined modulus of elasticity different from said first predetermined modulus of elasticity to provide for differentiated longitudinal flexure of the foot member upon application of walking pressure, said heel and midfoot sections being configured for detachable combination via a coupling joint to provide for selected modular adaption of the foot member, said coupling joint including a generally vertical rigid pin defining a generally vertical axis about which said midfoot section pivots relative to said heel section and a generally vertical resilient pin interconnecting said midfoot and heel sections to resiliently limit pivot about said generally vertical axis of said midfoot section relative to said heel section; and an ankle member coupled with said foot member, said ankle member being capable of rotation about an axis which is substantially perpendicular to a longitudinal line connecting said midfoot and heel sections of said foot member.

2. The prosthetic device of claim 1 wherein said midfoot section is more resilient than said heel section.

3. The prosthetic device of claim 1 wherein said foot member further includes a toe section removably coupled with said midfoot section and extending forwardly from said midfoot section opposite said heel section.

4. The prosthetic device of claim 3 wherein said midfoot section is more resilient than said heel section and said toe section is more resilient than said midfoot section.

5. The prosthetic device of claim 1 wherein said resilient pin is formed of rubber.

6. The artificial ankle and foot of claim 1 wherein said resilient pin is formed of foam rubber.

7. A lower extremity prosthetic device comprising:

a foot member including a rearward heel section and a midfoot section which extends forwardly therefrom, said heel and midfoot sections being configured for detachable engagement with one another via a coupling joint and said heel section including a pair of spaced arms with facing convex washers;

an ankle member coupled with said foot member, said ankle member including a shaft extending between said arms and a bearing arrangement with a resilient annular body interposed less resilient inner and outer annular shells to provide for backward/forward rotation of said ankle member about said shaft to define an axis which is substantially perpendicular to a longitudinal line connecting said midfoot and heel sections of said foot member, said bearing arrangement being mounted between said convex washers to provide for side-to-side pivot of said ankle member;

a first resilient cushion interposed between said ankle and foot members in an area rearward of said axis to bias the ankle in a first rotational direction, said cushion nominally defining two or more grooves which extend laterally about said cushion to provide a bellows-shaped cushion which compresses without substantial deformation of said foot member; and a second resilient cushion interposed between said ankle and foot members forwardly of said axis to oppose said first resilient cushion bias.

8. The prosthetic device of claim 7 wherein said first resilient cushion is formed of rubber.

9. The prosthetic device of claim 7 wherein said first resilient cushion is formed of foam rubber.

10. The prosthetic device of claim 7 wherein said first resilient cushion includes a lever portion which tends to urge said ankle member away from said foot member.

* * * * *